(12) United States Patent
Norman et al.

(10) Patent No.: US 8,273,364 B2
(45) Date of Patent: Sep. 25, 2012

(54) PLANT REMEDIATION

(75) Inventors: Louis Jack Norman, Binghamton, NY (US); Kelly Green, Phoenix, NY (US)

(73) Assignee: Kelly Green, Phoenix, NY (US)

( * ) Notice: Subject to any disclaimer, the term of this patent is extended or adjusted under 35 U.S.C. 154(b) by 154 days.

(21) Appl. No.: 12/410,242

(22) Filed: Mar. 24, 2009

(65) Prior Publication Data

US 2009/0246297 A1    Oct. 1, 2009

Related U.S. Application Data

(63) Continuation-in-part of application No. 11/957,153, filed on Dec. 14, 2007, now abandoned.

(51) Int. Cl.
    *A01N 25/00*      (2006.01)
    *A01N 59/00*      (2006.01)
    *A01N 55/10*      (2006.01)

(52) U.S. Cl. ........ 424/405; 424/722; 424/724; 504/187; 504/193

(58) Field of Classification Search .......... None
See application file for complete search history.

(56) References Cited

U.S. PATENT DOCUMENTS

| | | | |
|---|---|---|---|
| 5,183,477 A * | 2/1993 | Masuda | 47/58.1 R |
| 5,780,390 A * | 7/1998 | Hintz et al. | 504/365 |
| 5,843,866 A | 12/1998 | Parker et al. | |
| 6,746,988 B2 * | 6/2004 | Hopkinson et al. | 504/127 |

OTHER PUBLICATIONS

Sil-Matrix fungicide/miticide/insectide available on the Internet Nov. 13, 2006; 6 pages.*
Uriarte, et al., "Effect of Soluble Silica on Brown Patch and Dollar Spot of Creeping Bentgrass," Journal of Plant Nutrition, vol. 27, No. 2, 2004, p. 325-339.
International Preliminary Report on Patentability, dated Jun. 24, 2010, received in international patent application No. PCT/US08/086893, 6 pgs.

* cited by examiner

*Primary Examiner* — Ernst Arnold
(74) *Attorney, Agent, or Firm* — Harris Beach PLLC

(57) ABSTRACT

A method for treating diseased plants, such as turf and trees, includes mixing a quantity of a plant remediation composition with water and applying the plant remediation composition to the diseased plants. The plant remediation composition may include from about 70 up to about 90 volume percent of a potassium silicate, up to 10 volume percent of a sodium silicate, from about 0.25 to about 3.0 volume percent of a surfactant, from about 0.25 to about 3.0 volume percent of a polyol, and the remaining volume percent water. The plant remediation composition may be used to treat plant molds, bacteria and fungi, such as Anthracnose, Fairy Ring, Brown Patch, Dollar Spot, and Snow Mold, and may also be used to prevent and remediate insect infestations.

16 Claims, No Drawings

PLANT REMEDIATION

CROSS-REFERENCE TO RELATED APPLICATIONS

This application is a continuation-in-part of the following application, which is herein incorporated by reference:

U.S. patent application Ser. No. 11/957,153, filed 14 Dec. 2007, and entitled "Turf Mold Remediation",

FIELD OF INVENTION

The present invention relates to mold remediation and more specifically to turf mold remediation.

BACKGROUND

Turf mold, algae and fungus may be devastating to grass in parks, cemeteries and golf courses. For example, the quality of a golf course is often measured by the quality of the grass, particularly on the greens. Many golf courses treat the greens with various fertilizers, herbicides and pesticides to maintain the quality of the greens and inhibit the growth and reproduction of various turf molds, algae and fungi. It has been noted that golf courses may apply pesticides at higher concentrations per acre than any other land use. These high concentrations of use cause concern of runoff contamination to surrounding waterways, wildlife and communities.

Specifically, the runoff of fertilizers, herbicides and pesticides is thought to effect the biochemical oxygen demand of any surrounding bodies of water and environments. Biochemical oxygen demand is the amount of oxygen required by aerobic microorganisms to decompose the organic matter in water, such as that polluted by sewage and organic chemicals, and is used as a measure of the degree of water pollution. Natural organic debris and organic waste from agricultural and urban runoff are a food source for water-borne bacteria. The bacteria consume these organic materials using dissolved oxygen in the water, thus reducing the dissolved oxygen present for fish and other aquatic life. The more organic debris and waste there is in the water, such as hydrocarbons from the fertilizers, herbicides and pesticides used on the golf courses, the more food there is available to the bacteria. The more food there is available to the bacteria, the more oxygen the bacteria will consume, thereby depleting the oxygen available for any fish, plants and other aquatic life that relies on that body of water.

Further, the various fertilizers, herbicides and pesticides often used by golf courses, parks and other open land areas contain other dangerous chemicals that can build up in the soil and runoff into nearby waterways, thereby polluting both the land and the water. For example, pesticides can be toxic, and build up because of their slow degradation time. Also, many herbicides and pesticides are toxic to aquatic life.

SUMMARY

The present invention provides a more environmentally neutral compound and method to inhibit the growth and reproduction of various turf molds, algae and fungi.

In general, in one aspect, the invention features a turf mold remediation composition. The turf mold remediation composition may include from about 30 to about 50 volume percent of a potassium silicate, from about 0.25 to about 2.0 volume percent of a surfactant; from about 0.25 to about 2.0 volume percent of a polyol, and from about 46.0 to about 69.5 volume percent water. Each of the these components are present as volume percentages of the total turf mold remediation composition.

In various embodiments, the potassium silicate may be present from about 35 to about 45 volume percent, the surfactant may be present from about 0.50 to about 1.5 volume percent, and the polyol is present from about 0.50 to about 1.5 volume percent.

In certain embodiments, the polyol is a polyethylene glycol.

In general, in another aspect, the invention features a turf mold remediation composition including about 41 volume percent of a potassium silicate, about 1.0 volume percent of a surfactant, about 1.0 volume percent of a polyol, and about 57 volume percent of water. Each of the these components are present as volume percentages of the total turf mold remediation composition.

In general, in another aspect, the invention features a method for treating diseased plants including mixing a quantity of the plant remediation composition with water and applying the plant remediation composition and water mixture to the diseased plants.

In various embodiments, about four fluid ounces of the plant remediation composition are mixed with about two gallons of water. In embodiments, the diseased plants are turf grass. In other embodiments, the diseased plants may be agricultural crops, sod or trees. In further embodiments, the disease may be a turf mold or a fungus.

The invention may be implemented to realize one or more of the following advantages. The turf mold remediation composition may be applied to any grass or plant to inhibit the growth and reproduction of various molds, algae, bacteria and fungi, including those spread by various insects. Further, the turf mold remediation composition may kill various insects and prevent the insects' eggs from developing. The potassium silicate in the turf mold remediation composition may provide nutrients to the grass or plant to which it is applied, which will further enable the grass or plant to naturally fight against the mold, algae or fungus. However, the turf mold remediation composition may have minimal if any effect on the biochemical oxygen demand of any surrounding water because it contains minimal organic components. Because of the minimal amount of organic components, in the form of hydrocarbons, and the amount of dilution to the turf mold remediation composition during application, any organic component is likely to be consumed by the bacteria found in the surrounding soil.

The turf mold remediation composition may also be provided containing little or no volatile organic compounds or solvents, and producing no greenhouse gases. Further, the predominant component of the turf mold remediation composition, a soluble silicate, is environmentally inert. Further still, the area to which the turf mold remediation composition is applied may be used immediately after application since the turf mold remediation composition may be non-toxic and safe to handle. Similarly, because the turf mold remediation composition may be non-toxic, minimal precautions are needed by those who apply the turf mold remediation composition.

Other features and advantages of the invention are apparent from the following description, and from the claims.

DETAILED DESCRIPTION

The turf mold remediation composition broadly includes from about 30 to about 50 volume percent of a soluble potassium silicate, from about 0.25 to about 2 volume percent of a surfactant, from about 0.25 to about 2 volume percent of a polyol, and the remainder (e.g., from about 46 to about 69.5%) water. This concentration of turf mold remediation composition may be further diluted in water prior to application, as discussed further below.

Soluble silicates are systems containing varying proportions of silica and an alkali metal or quaternary ammonium ion. The most common and most widely used soluble silicates are those of sodium and potassium. Ordinarily, soluble silicates can be produced over a wide range of stoichiometric and non-stoichiometric compositions and are distinguished by the ratio of silica to alkali metal. The ratio is generally expressed as the weight percent ratio of silica to alkali-metal oxide.

A preferred soluble silicate for the turf mold remediation composition is potassium silicate. Usable commercial potassium silicates includes KASIL 1 from PQ Corporation of Valley Forge, Pa. It is believed that the silicate lattice inhibits the growth and reproduction of the targeted mold, algae or fungus. When the mold, algae or fungus is treated, the grass seeks nutrients to grow and further combat the mold, algae or fungus, which is provided by the potassium in the silicate. The potassium silicate may not affect the biochemical oxygen demand on any nearby water because it is not an organic based chemical.

Soluble potassium silicate in the turf mold remediation composition may be present at a level from about 30 to about 50%, based on the total volume of the final turf mold remediation composition. Preferably, the ingredient is present at a level from about 35 to about 45 volume %. Most preferably, about 41 volume % of the soluble potassium silicate may be used.

The next ingredient used for the turf mold remediation composition is a surfactant. A surfactant is an organic compound consisting of two parts: (1) A hydrophobic portion, usually including a long hydrocarbon chain; and (2) a hydrophilic portion which renders the compound sufficiently soluble in water or other polar solvents. The combination of hydrophobic and hydrophilic portions in a surfactant render the surfactant surface-active and thus able to concentrate at the interface between a surfactant solution and another phase such as soil, plant roots and the mold, algae or fungus to be treated.

Preferred surfactants for the turf mold remediation composition are anionic surfactants, such as esters of organo-phosphoric acid. Commercially, organo-phosphoric acid ester is sold under the tradename "T MULZ," No. 598, available from Harcros Chemicals Inc., Kansas City, Kans. This commercial product has a boiling point of 290° F.@760 mm Hg. The specific gravity (H(2)0=1) is 1.111@77° F. The pH of a 1% aqueous solution of this product is in the range of 2 to 3. It is a clear amber liquid.

The surfactant in the turf mold remediation composition may be present at a level from about 0.25 to about 2%, based on the total volume of the final turf mold remediation composition. Preferably, this ingredient is present at a level from about 0.50 to about 1.5 volume %. Most preferably, about 1 volume % of the anionic surfactant may be used.

The next ingredient used for the turf mold remediation composition is a polyol. Known polyols include different glycols, glycerins, sugars, and polyethylene glycols. These polyols may be compatible and miscible with alkali-metal silicate solutions. The preferred polyol for the turf mold remediation composition is polyethylene glycol, and more specifically polyethylene glycol 400. Polyethylene glycol 400 has a molecular weight of 400; a specific gravity of 1.12 g/cm$^3$; and a freezing point in air of about 6° C. (760 mm Hg).

It is completely soluble in water. Polyethylene glycol is often used in consumer products, such as shampoo. Commercially, polyethylene glycol 400 NF can be purchased from Univar USA of Redmond, Wash.

Polyol in the turf mold remediation composition is present at a level from about 0.25 to about 2%, based on the total volume of the final turf mold remediation composition. Preferably, polyol is present at a level from about 0.50 to about 1.5 volume %. Most preferably, about 1 volume % of the polyethylene glycol may be used.

While the surfactant and polyol are both hydrocarbon based, and thus may affect the bio-chemical oxygen demand of any nearby water, the low concentration of each may enable bacteria in the soil to consume most, if not all, of the organic component before it even reaches any body of water. Further, as described below, because the turf mold remediation composition in the concentrations described are typically diluted in water when it is applied to the effected area, the concentration of these organic components will be further diluted.

Water forms the remainder of the turf mold remediation composition. It may be present from about 46 to about 69.5%, based on the total volume of the final turf mold remediation composition. Preferably, it may be present from about 52 to about 64 volume %. Most preferably, it may be present in an amount of about 57 volume %.

The turf mold remediation composition may be made by adding with agitation, about 1%, based on the total volume of the final turf mold remediation composition, of an organo phosphoric acid ester anionic surfactant, T MULZ 598, to water present in an amount of about 57 volume % to obtain a first substantially homogeneous resultant mixture. Then, with agitation, about 1 volume % of polyethylene glycol may be added to the first resultant mixture to obtain a second substantially homogeneous resultant mixture. Finally, about 41 volume % of potassium silicate may be added, accompanied by agitation, to the second resultant mixture to give a substantially homogeneous turf mold remediation composition.

The following composition is representative of the turf mold remediation composition.

| Component | % by volume |
| --- | --- |
| Potassium Silicate | 41 |
| T MULZ 598 Surfactant | 1 |
| Polyethylene Glycol | 1 |
| Water | 57 |

This turf mold remediation composition is stable and effectively inhibits the growth and reproduction of various molds, algae and fungi on plants and grass, while providing nutrients to the plants and grass. For example, it can be used to inhibit the growth of turf mold on a golf course.

Specifically, to inhibit the growth and reproduction of turf mold on a golf course, four (4) fluid ounces of the turf mold remediation composition may mixed with two (2) gallons of water and applied to the affected grass. Typically, four fluid ounces will treat approximately 1000 square feet of grass.

In an experimental study, turf mold remediation composition was tested against anthracnose, a common disease that affects various turf used on golf course putting greens. Sample turf plots having a mix of creeping bentgrass and annual bluegrass were prepared. Each turf plot was mowed three times a week at 0.5 inches and received weekly fertilization of ammonium sulfate, monoammonium phosphate and potassium sulfate. Starting on June 14, each turf plot was treated with one of various anti-fungal treatments. Some were treated with the turf mold remediation composition of the present invention and some were treated with different ones of various commercially available products at various intervals, such as 7-day, 14-day, 21-day or 28-day intervals. Different concentrations of the each were also tested by mixing different amounts of the anti-fungal treatments in 2-gallons of water. Each turf plot was examined and rated for the percentage of anthracnose present in the samples at two different times—July 22nd and August 18th. The turf mold remediation composition of the present invention worked at least as well as, and often better than, the other commercially available products. Several examples of the results are given below in Table 2. As can be seen from the July 22nd rating, the percentage of anthracnose in the turf plots ranged from 0% to 21.7%, with the turf mold remediation composition of the present invention resulting in 0% to 5%. For the August 18th rating, the percentage of anthracnose in the turf plots ranged from 3.3% to 71.7%, with the turf mold remediation composition of the present invention resulting in 8.3% to 25%. Thus, the turf mold remediation composition of the present invention worked better than most of the other commercially available products, but is also environmentally friendly.

applied at a rate of ¹⁄₁₀th pound per 1000 square feet. On each of these putting greens, the Dollar Spot infestation was eradicated within 72 hours after the application of the turf mold remediation composition.

The turf mold remediation composition of the present invention has also shown to be effective against other common molds and fungi found on golf courses, such as Fairy Ring, Brown Patch, and Snow Mold.

It is to be understood that the foregoing description is intended to illustrate and not to limit the scope of the invention, which is defined by the scope of the appended claims. Other embodiments are within the scope of the following claims. For example, while application to golf course turf has been described, the turf mold remediation composition may work equally well to treat other turfs, such as on football fields, baseball fields, soccer fields, playgrounds or sod farms.

Further, it may be used for agricultural applications, such as for treating food crops. For example, the turf mold remediation composition has been shown to effectively prevent and treat various mold, fungus and bacteria in fruit trees, such as Canker in orange trees. The turf mold remediation composition may also work on other molds, fungus and bacteria, including Yellow and Black Sigatoka on banana trees. In

TABLE 1

% Anthracnose

| | | | Date of Rating | |
|---|---|---|---|---|
| Sample | Product | Interval | 22-Jul | 18-Aug |
| 1 | Standard Fertilizer | 7 d | 8.3 | 33.3 |
| 2 | Spectator 41.8% EC (0.37 oz.) | 14 d | 1.7 | 16.7 |
| 3 | Spectator 41.8% EC (0.72 oz.) | 28 d | 1.7 | 8.3 |
| 4 | 18 Plus Flowable 23.3% | 14 d | 0.0 | 3.3 |
| 5 | Manicure (Chlorothalonil) | 14 d | 5.0 | 23.3 |
| 6 | Emerald (0.13 oz.) | 28 d | 1.7 | 30.0 |
| 7 | Emerald (0.18 oz.) | 28 d | 1.7 | 18.3 |
| 8 | EcoGuard | 7 d | 21.7 | 71.7 |
| 9 | Earthworks Tea | 7 d | 1.7 | 25.0 |
| 10 | North Country Tea | 7 d | 0.0 | 8.3 |
| 11 | Manicure (1 oz.) + Actigard | 14 d | 6.7 | 25.0 |
| 12 | Manicure (0.5 oz.) + Actigard | 14 d | 11.7 | 48.3 |
| 13 | Griggs Bros II + Manicure (1 oz.) | 14 d | 1.7 | 21.7 |
| 14 | Super Bio Soil Life (Liquid) | 21 d | 5.0 | 25.0 |
| 15 | Turf Shield + MacroSorb | 7 d | 0.0 | 13.3 |
| 16 | EcoGuard + Earthworks Tea | 7 d | 20.0 | 53.3 |
| 17 | EcoGuard + North Country Tea | 7 d | 10.0 | 48.3 |
| 18 | EcoGuard + Turf Shield + MacroSorb | 7 d | 12.3 | 41.7 |
| 19 | EcoGuard + Super Bio Soil Life | 7 d/21 d | 10.0 | 8.3 |
| 20 | EcoGuard + Earthworks + Turf Shield + Macro Sorb | 7 d | 11.7 | 43.3 |
| 21 | EcoGuard + Earthworks + Super Bio Soil Life | 7 d/21 d | 13.3 | 56.7 |
| 22 | EcoGuard + Earthworks + Turf Shield + MacroSorb + Super Bio Soil Life | 7 d/21 d | 10.0 | 46.7 |
| 23 | EcoGuard + North Country + Actigard | 7 d | 8.3 | 38.3 |
| 24 | EcoGuard + North Country + Super Bio Soil Life | 7 d/21 d | 5.0 | 45.0 |
| 25 | EcoGuard + North Country + MacroSorb + Super Bio Soil Life | 7 d/21 d | 13.3 | 50.0 |
| 26 | turf mold remediation composition (0.25 oz.) | 7 d | 3.3 | 21.7 |
| 27 | turf mold remediation composition (0.50 oz.) | 7 d | 0.0 | 8.3 |
| 28 | turf mold remediation composition (1 oz.) | 14 d | 5.0 | 26.7 |
| 29 | turf mold remediation composition (2 oz.) | 14 d | 1.7 | 23.3 |
| 30 | turf mold remediation composition (4 oz.) | 14 d | 0.0 | 25.0 |
| | Least Significant Difference (p = 0.05) | | 12.3 | 34.7 |

In another experimental study, the turf mold remediation composition of the present invention was applied to several putting greens effected by a disease known as Dollar Spot. The turf mold remediation composition was applied at a rate of four ounces per 1000 square feet. Following the application of the turf mold remediation composition, nitrogen was addition, the turf mold remediation composition has been shown to kill various insects that attack crops, such as the Asian Citrus Psyllid, which attacks orange trees. The Asian Citrus Psyllid is a major problem for citrus grows as these insects attack the orange trees, damaging the fruit and spreading Huanglongbing, a crop destroying disease known as Citrus Greening. The turf mold remediation composition may not only kill active insect infestations, but may also stick to the leaves and fruit of an orange tree to provide a protective coating against insect attacks before they occur. While the above disclosed compositions may provide the remediation and preventive protection against disease and insect infestation, a further composition may include higher silicate concentrations and the addition of a soluble sodium silicate, which may help the turf mold remediation composition adhere better to the tree or food crop. An exemplary composition may include:

| Component | % by volume |
|---|---|
| Potassium Silicate | 70 |
| Sodium Silicate | 10 |
| T MULZ 598 Surfactant | 1 |
| Polyethylene Glycol 400 | 1 |
| Water | 18 |

When mixing this exemplary turf mold remediation composition, the materials may be at least at room temperature (e.g., 65-75° F.). This exemplary turf mold remediation composition may be mixed by first slowly adding the 1% by volume of T-Mulz 598 surfactant to the 18% by volume of water while slowly mixing until the mixture is clear, which indicates that the surfactant has been sufficiently dissolved. The 1% by volume of polyethylene glycol 400 may then be mixed into the resultant mixture of water and surfactant. The 10% by volume of sodium silicate may then be added and mixed until completely clear. Finally, 70% by volume of potassium silicate may be added in small amounts while mixing thoroughly between each addition to ensure good dilution of the potassium silicate.

While this composition is a preferred formulation for application to trees and other plant crops, it is to be understood other formulations may be used. For example, when using both the soluble potassium silicate and soluble sodium silicate, the surfactant and the polyol may each be added up to a concentration of about 3% by volume. With higher concentrations of the surfactant and the polyol, the sodium silicate may only go into the mixture up to about 9% by volume. In such a mixture, the soluble potassium silicate may be added up to about 30% by volume, and the water up to about 55% by volume.

In compositions not using the soluble sodium silicate, and lower concentrations of the surfactant and polyol, for example about 1% by volume, the soluble potassium silicate may be added up to about 90% by volume.

Further, as explained above, the turf mold remediation composition may be applied by mixing the turf mold remediation composition with water before application. For example, when the turf mold remediation composition is mixed with a total soluble silicate concentration, either with or without the sodium silicate, under 40% by volume, the turf mold remediation composition may be diluted by mixing one part turf mold remediation composition with up to about five parts water. In another example, when the turf mold remediation composition is mixed with a total soluble silicate concentration over 75% by volume, the turf mold remediation composition may be diluted by mixing one part turf mold remediation composition with up to about fifteen parts water.

Also, while the above describes the application of the turf mold remediation composition alone, the turf mold remediation composition may be applied in conjunction with other anti-fungal or anti-mold products.

What is claimed is:

1. A method for treating plants comprising:
  mixing a quantity of a plant remediation composition with water, wherein the plant remediation composition comprises
    about 70 up to about 90 volume percent of the total plant remediation composition of a potassium silicate;
    up to about 10 volume percent of the total plant remediation composition of a sodium silicate;
    from about 0.25 to about 3.0 volume percent of the total plant remediation composition of a surfactant;
    from about 0.25 to about 3.0 volume percent of the total plant remediation composition of a polyol;
    the remaining volume percent of the total plant remediation composition water; and
  applying the plant remediation composition and water mixture to the plants.

2. The method of claim 1 wherein the plant remediation composition comprises
  about 70 volume percent of the total plant remediation composition of potassium silicate;
  about 10 volume percent of the total plant remediation composition of sodium silicate;
  about 1.0 volume percent of the total plant remediation composition of surfactant; and
  about 1.0 volume percent of the total plant remediation composition of polyol.

3. The method of claim 1 wherein mixing the quantity of plant remediation composition with water comprises mixing about one part of the plant remediation composition with about fifteen parts water.

4. The method of claim 1 wherein mixing the quantity of plant remediation composition with water comprises mixing about one part of the plant remediation composition with about five parts water.

5. The method of claim 1 wherein the plants are food crops.

6. The method of claim 5 wherein the food crop is a fruit producing plant.

7. The method of claim 1 wherein the plants are selected from the group consisting of agricultural crops, sod and trees.

8. The method of claim 7 wherein the agricultural crops are selected from the group consisting of orange trees, banana trees, grape vines, fruit trees, nut-bearing trees, and vegetable plants.

9. The method of claim 1 wherein the plant remediation composition is applied to treat one of a fungus, a mold, a bacteria, an algae and insects.

10. The method of claim 1 wherein the plant remediation composition is applied to kill insects.

11. The method of claim 1 wherein the plant remediation composition provides a protective layer on the plants.

12. The method of claim 1 wherein the polyol is a polyethylene glycol having a molecular weight of about 400.

13. The method of claim 1 wherein the surfactant is an ester of organo-phosphoric acid.

14. The method of claim 1 wherein the plants are diseased plants.

15. A plant remediation composition comprising:
  about 70 up to about 90 volume percent of the total plant remediation composition of a potassium silicate;
  up to about 10 volume percent of the total plant remediation composition of a sodium silicate;
  from about 0.25 to about 3.0 volume percent of the total plant remediation composition of a surfactant;
  from about 0.25 to about 3.0 volume percent of the total plant remediation composition of a polyol;
the remaining volume percent of the total plant remediation composition water.

16. The plant remediation composition of claim 15 comprising:
- about 70 volume percent of the total plant remediation composition of potassium silicate;
- about 10 volume percent of the total plant remediation composition of sodium silicate;
- about 1.0 volume percent of the total plant remediation composition of surfactant; and
- about 1.0 volume percent of the total plant remediation composition of polyol.

* * * * *